United States Patent [19]
Krzystowczyk et al.

[11] Patent Number: 5,663,469
[45] Date of Patent: *Sep. 2, 1997

[54] PRODUCTION OF VINYLIDENE OLEFINS

[75] Inventors: Douglas H. Krzystowczyk; Kaung-Far Lin, both of Baton Rouge, La.

[73] Assignee: Amoco Corporation, Chicago, Ill.

[*] Notice: The term of this patent shall not extend beyond the expiration date of Pat. No. 5,625,105.

[21] Appl. No.: 596,812

[22] Filed: Feb. 5, 1996

[51] Int. Cl.$^6$ .................................................. C07C 2/26
[52] U.S. Cl. .............................. 585/503; 585/511; 585/512
[58] Field of Search ......................................... 585/503, 511, 585/512

[56] References Cited

U.S. PATENT DOCUMENTS

| | | | |
|---|---|---|---|
| 4,155,946 | 5/1979 | Sato et al. | 585/513 |
| 4,709,112 | 11/1987 | Sato et al. | 585/513 |
| 4,795,851 | 1/1989 | Frame et al. | 585/512 |
| 4,973,788 | 11/1990 | Kaung-Far Lin et al. | 585/511 |
| 5,124,465 | 6/1992 | Allen et al. | 556/190 |
| 5,516,958 | 5/1996 | Schaerfl, Jr. et al. | 585/511 |

OTHER PUBLICATIONS

Ziegler, et al., *Justus Liebigs Ann. Chem.*, vol. 629, pp. 1–74 (Mar. 1960) Translation.
*The Use of Aluminum Alkyls in Organic Synthesis*, Ethyl Corporation, pp. 1–75, (2nd Printing, Mar., 1977).

Primary Examiner—Jacqueline V. Howard
Attorney, Agent, or Firm—Joseph DiSalvo; Stephen L. Hensley

[57] ABSTRACT

Vinylidene olefin can be formed in good yield and high selectivity in much shorter reaction periods than found critical heretofore. The process involves dimerizing vinyl olefin with at least one trialkylaluminum compound as the catalyst component charged to the reaction vessel. These materials are charged to the reactor so that it contains in the range of 0.001 to 0.5 mol of trialkylaluminum per mol of the initial vinyl olefin. The reaction is performed at a temperature in the range of 100° to 200° C. for a period of time sufficient to convert 10 to 99% by weight of the initial vinyl olefin to a different product with at least 80 wt % vinylidene dimer selectivity. In conducting the process the liquid reaction mixture is in direct contact with a nickel-containing metal alloy surface for at least one hour at a temperature above about 50° C., and (ii) at least one acetylenic hydrocarbon is added to the mixture prior to such contact in an mount at least sufficient to inhibit double bond isomerization in the reaction mixture but insufficient to inhibit formation of the vinylidene dimer. The acetylenic hydrocarbon also overcomes the devastating effect nickel impurities in the feed or in residues in the reactor have on dimer selectivity.

36 Claims, No Drawings

PRODUCTION OF VINYLIDENE OLEFINS

TECHNICAL FIELD

This invention relates to an improved process enabling the production of vinylidene olefins in good yields with high selectivities.

BACKGROUND

Vinylidene olefin, which are branched monoolefins having the structure $(R^1)(R^2)C=CH_2$ where $R^1$ and $R^2$ are the same or, more usually, different alkyl groups, are of commercial importance as raw materials for use in producing-double tailed oxo alcohols and other functionalized derivatives, used in the manufacture of detergents, surfactants, specialty agricultural chemicals, and fuel or lubricant additives. Vinylidene olefins can be produced by dimerizing vinyl olefins.

U.S. Pat. No. 4,155,946 to Sato, Noguchi and Yasui discloses a process for dimerizing lower α-olefins in which the catalyst system is formed from (1) a trialkylaluminum compound, (2) a salt or complex of nickel, (3) a trivalent phosphorus compound selected from specified groups, and (4) a halogenated phenol.

U.S. Pat. No. 4,709,112 to Sato, Ikimi, Tojima and Takahashi describes a process for dimerizing lower α-olefins which uses a catalyst system formed from (1) a trialkylaluminum compound, (2) an organic salt or complex of nickel, (3) a trivalent phosphorus compound selected from specified groups, (4) a fluorinated isopropanol, and (5) a catalyst co-activator selected from specified types of halogenated compounds.

U.S. Pat. No. 4,973,788 to Lin, Nelson and Lanier describes a process for dimerizing a vinyl olefin monomer at a selectivity of at least 85 mol percent. This is accomplished by use of a catalyst which consists essentially of 0.001–0.04 mols of trialkylaluminum per mol of vinyl olefin, and conducting the reaction at a temperature in the range of about 100°–140° C. for a time sufficient to convert at least 80 mol percent of the initial vinyl olefin to a different product. The reaction rate under these conditions is quite slow, and thus a long reaction time is required. For example it is pointed out that the time required for 90 percent conversion at 120° C. with 0.043 mols of aluminum alkyl catalyst per mol of initial vinyl olefin is about 94 hours, and that with 0.017 mols of the catalyst per mol of initial vinyl olefin the time required at 120° C. is about 192 hours. It is also shown in the patent that although the reaction is faster at 172° C. compared to 120° C., the selectivity to vinylidene dimer is only 71 weight percent compared to 90 weight percent with the same catalyst concentration but at 120° C.

The vinylidene dimerization reaction with a trialkylaluminum catalyst involves the catalytic interaction (perhaps transitory coupling) between the vinyl olefin and the aluminum alkyl. As indicated in U.S. Pat. No. 4,973,788, supra, the dimerization is effected at temperatures of 100°–140° C. It has now been found that at these and higher temperatures, isomerization of vinyl olefin to internal olefin can occur. This competitive reaction reduces dimerization product yield, because these isomers do not further react to produce the desired vinylidene olefin product.

During olefin displacement reactions, isomerization of linear 1-olefins is known to occur when trace amounts of certain metals, especially nickel, react with the aluminum alkyl catalysts. For example, Ziegler et at., *Justus Liebigs Ann. Chem.* Volume 629 at pages 25 and 62 (1960) mentioned using phenyl acetylene to reduce isomerization in olefin displacement reactions catalyzed by nickel. To the same general effect is U.S. Pat. No. 5,124,465 to Allen, Anderson, Diefenbach, Lin, Nemec, Overstreet and Robinson. In *The Use of Aluminum Alkyls in Organic Synthesis*, Ethyl Corporation, page 53 (1977), it is stated "The isomerization of the α-olefin by the nickel catalyst can be suppressed by addition of small amounts of acetylene hydrocarbons, but by and large this modification of the displacement has not been developed to perfection."

It would be extremely desirable to be able to achieve high selectivity to vinylidene dimer in a dimerization process without requiring use of the extremely long reaction periods deemed necessary in accordance with the process of U.S. Pat. No. 4,973,788 and without need for multicomponent catalyst systems such as described in U.S. Pat. Nos. 4,155,946 and 4,709,112, especially if the dimerization reaction can be conducted using nickel-containing reaction vessels, transfer lines, and like reactor auxiliaries, and without concern about possible presence of trace amounts of nickel-containing impurities in the feeds to, or on the walls of, the reactor.

The present invention has accomplished this goal, and made it possible to achieve all of these highly beneficial results.

SUMMARY OF THE INVENTION

It has been found that, unfortunately, when effecting dimerization of vinyl olefin to vinylidene olefin using an aluminum alkyl catalyst, the presence of trace amounts of nickel can dramatically decrease yields of the desired vinylidene olefin and greatly increase the rates at which competitive double bond isomerization reactions occur.

It has also been found pursuant to this invention that nickel-induced double bond isomerization during the dimerization reaction can be inhibited without adversely affecting the dimerization reaction itself, and that vinylidene dimer can be produced with high selectivity and yield without requiring the long reaction periods which were deemed critical in the process of U.S. Pat. No. 4,973,788, all without need for multicomponent catalyst systems of the type described in U.S. Pat. Nos. 4,155,946 and 4,709,112. This can be accomplished by producing vinylidene olefin using an embodiment of this invention which comprises heating at one or more dimerization temperatures in the range of about 100° C. to about 200° C., a mixture formed by mixing together at a temperature below about 50° C. and in any sequence (i) at least one vinyl olefin, (ii) at least one trialkylaluminum, and (iii) at least one acetylenic hydrocarbon in proportions in the range of about 0.001 to about 0.5 mol of trialkylaluminum per mol of the vinyl olefin, and a passivating mount in the range of up to about 5000 parts by weight of acetylenic hydrocarbon per million parts by weight of said mixture, the amount of the acetylenic hydrocarbon being at least sufficient to prevent more than 3% loss of dimer selectivity due to the presence of nickel impurities in said mixture and/or nickel-containing surfaces with which said mixture comes in contact prior to or during the dimerization reaction.

Another embodiment of this invention is a process which comprises (a) charging a reaction vessel with vinyl olefin and at least one trialkylaluminum compound as dimerization catalyst in a ratio in the range of 0.001 to 0.5 mol of trialkylaluminum per mol of the initial vinyl olefin, and (b) heating the mixture at one or more temperatures in the range of about 100° to about 200° C. for a period of time sufficient to convert from 10 to about 99% by weight of the initial vinyl olefin to a different product with at least 80% vinylidene dimer selectivity, with the provisos that in conducting the process the liquid mixture is maintained in direct contact with a nickel-containing metal alloy surface for at least one hour at a temperature above about 50° C., and that at least one acetylenic hydrocarbon is added to the mixture prior to said contact in an amount at least sufficient to inhibit double bond isomerization in the reaction mixture but insufficient to inhibit formation of the vinylidene dimer. Stated another way, the amount of acetylenic hydrocarbon added to the reaction mixture is at least sufficient to overcome the deleterious effect of the nickel present on dimer selectivity.

So far as is known, this invention represents the first time consideration has been focused upon the interrelationships among reaction conditions, materials of construction, and competitive reaction rates in the conduct of an olefin dimerization process.

As noted above, it has been found that when a vinyl olefin is heated in the presence of a trialkylaluminum dimerization catalyst to a temperature at which dimerization takes place, competitive reactions can and generally do occur. For example, in addition to the desired dimer formation via the Markovnikov route, vinyl olefin can be also be dimerized to deep internal olefin dimer via the competitive anti-Markovnikov route. Also, vinyl olefin can be isomerized to internal isomer olefin via aluminum hydride route or by other known mechanisms. Moreover, it has now been found that the presence of trace amounts of nickel such as can be leached from surfaces of the reactor and of reactor auxiliaries such as piping, valves, agitators, and the like can have a profound deleterious effect upon the outcome of the dimerization reaction. In a dimerization process competitive internal olefin formation adversely affects dimer selectivity, and deep internal olefin dimer formation adversely affects final vinylidene olefin purity. However, despite the existence of such adverse competitive reactions, the practice of this invention now makes possible substantial enhancement of vinylidene dimer selectivity and suppression of nickel-induced isomerization to internal olefins.

Besides overcoming the devastating effects such contact of the hot reaction mixture with nickel surfaces can have on dimer selectivity when conducting a dimerization reaction, this invention also makes it possible to overcome the dire consequences on dimer selectivity resulting from the presence of nickel impurities that may be present as impurities in one or more materials fed to the reactor, and/or that may be present as residues or other types of contamination in the reactor or in auxiliaries, such as storage vessels, pumps, feed lines, agitators, valves, and the like.

Another feature of this invention is that although aluminum to hydrogen bonds serve as catalysts for isomerization of a 1-olefin to an internal olefin, and although the rate at which trialkylaluminum compounds dissociate into olefin and dialkylaluminum hydride rapidly increases with increasing temperature, the process of this invention enables the formation of vinylidene olefin products of almost as high a purity as the process of U.S. Pat. No. 4,973,788 in much shorter reaction periods.

Still another feature of the process of this invention is that it takes advantage of the exothermic nature of the olefin dimerization reaction. For example, the heat of reaction is about 20 Kcal per g mol of dimer formed. Thus by operating in the above temperature range, external energy requirements and costs are reduced, and when operating within particularly preferred temperature ranges (45° to 170° C.) such energy requirements and costs can be kept to a minimum.

There are three preferred general modes in which the process of this invention can be carried out. One such mode involves use of a single reactor commonly referred to as a "stirred pot reactor" in which the reaction is conducted with agitation on a batch basis. In another such mode the reactor comprises at least two closed vessels in which the reaction is conducted with agitation and continuous feed, the vessels being connected in series such that the feed rate to the first vessel, and the discharge rates from each vessel to the ensuing vessel, where there is an ensuing vessel, are substantially equal to each other. The third mode utilizes a single continuous elongated reactor in which the reaction is conducted with agitation on a continuous basis. When conducting the first or third of these modes it is particularly preferred to perform the reaction such that during at least 50 percent of the time that the reaction mixture is at a temperature above about 110° C.:

a) the vapor space in the reactor is in the range of 0 to 40 percent (more preferably in the range of 5 to 25 percent) of the total interior free space of the reactor, and b) the remainder of the free space in the reactor contains an inert atmosphere.

In the case of the second above mode of operation, the reaction is most preferably conducted such that during at least 50 percent of the time that the reaction mixture is at a temperature above about 110° C. in one or more of the vessels:

a) the vapor space in such vessels is in the range of 0 to 40 percent of the total interior free space of the vessels, and b) the remainder of the free space in the vessels contains an inert atmosphere.

In another preferred embodiment the process of this invention is conducted whereby the relationship among vinyl olefin conversion, reaction time and catalyst concentration is in accordance with the expression:

$$X = 1 - \exp\{-k[\text{alR}]t\}$$

where:

k is a rate constant which is a function of temperature, and is in terms of liters per gram mol per hour;

[alR] is the molar concentration of aluminum alkyl;

t is reaction time in hours; and

X is vinyl olefin conversion as defined by the expression:

$$1 - [Vi]/[Vi]_o$$

where:

[Vi] is the vinyl olefin molar concentration at time t; and

[Vi]$_o$ is the initial vinyl olefin molar concentration.

These and still other embodiments and features of this invention will become still further apparent from the ensuing description and appended claims.

FURTHER DETAILED DESCRIPTION OF THE INVENTION

The vinyl olefins used in the process can be one or more linear vinyl olefins or one or more branched chain vinyl olefins or any mixture of these. Minor amounts of internal and/or vinylidene monoolefins (e.g., up to 40 mol % of an olefin mixture) can be present in the initial vinyl olefin charged to the reactor. The amount of such internal and/or vinylidene olefins, if any, is of course excluded from consideration when calculating the mol ratios of catalyst to initial vinyl olefin used in the process. Typically the vinyl olefins used in the process will contain in the range of about 3 to about 30 or more carbon atoms per molecule. Preferably the initial vinyl olefin will contain in the range of 6 to 20, and still more preferably in the range of 8 to 16 carbon atoms per molecule. For some end use applications, it is desirable to use a substantially pure single vinyl olefin, such as 1-butene, 1-pentene, 1-hexene, 1-octene, 1-decene, or 1-tetradecene. For other end use applications mixtures of vinyl olefins are entirely suitable. In such case co-dimerization (a special case of dimerization) takes place.

Any trialkylaluminum compound can be used as the sole catalytic component charged to the dimerization reaction zone in the practice of this invention. Typically the alkyl groups will contain from 1 to 30 carbon atoms, and preferably in the range of 2 to about 18 carbon atoms each. Most preferred are trialkylaluminum compounds in which substantially all of the alkyl groups are a straight chain primary alkyl groups having in the range of from 2 to about 14 carbon atoms, such as triethylaluminum, tripropylaluminum, tributylaluminum, trihexylaluminum, trioctylaluminum, tris(decyl)aluminum, tris(tetradecyl) aluminum, and the like. Mixtures of aluminum trialkyls can be also used if desired. Changes in the composition or precise identity of the trialkylaluminum catalyst as compared to the composition and identity of the catalyst as charged to the reactor may occur as a matter of course during the conduct of the reaction, and it will be understood and appreciated that any such changes are within the scope of this invention since such changes, if they occur, are a natural consequence of the practice of the invention.

The hydride content, if any, of the aluminum trialkyl should be quite low, e.g., the aluminum trialkyl should have a maximum aluminum hydride equivalent of not more than about 0.8% In preferred embodiments the aluminum trialkyl as fed to the process is essentially hydride-free, i.e., the trialkylaluminum product contains, if any, a maximum of 0.10 wt % of aluminum hydride equivalent, and more preferably a maximum of 0.05 wt % of aluminum hydride equivalent, because the aluminum hydride bond can cause isomerization of 1-olefins to internal olefins.

It is preferred to conduct the process using in the range of about 0.001 to about 0.2 mol of trialkylaluminum per mol of the initial vinyl olefin, and even more preferably about 0.01 to about 0.05 mol of trialkylaluminum per mol of the initial vinyl olefin.

The one or more acetylenic hydrocarbons introduced into the reaction mixture before it is exposed to a nickel-containing metal surface at a temperature above about 50° C. can be a straight chain compound such as 1-hexyne or 2-hexyne, or a branched chain compound such as 4-methyl-1-pentyne or 5-methyl-1-hexyne, or a mixture or combination thereof. Any aliphatic, cycloalphatic or aromatic hydrocarbon having an acetylenic group may be suitable, especially if it has an immediately adjacent carbon atom that is substituted by two or three hydrogen atoms. Preferably the acetylenic hydrocarbon is a straight chain alkyne having from 4 to about 10 carbon atoms in the molecule, such as 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne, 4-octyne, and analogous nonynes and decynes. Mixtures of such alkynes having the same or different number of carbon atoms in the molecule can also be used. Most preferred are the individual hexyne isomers and mixtures of two or all three of such isomers. Hexyne has been found to be highly effective when added at low dosage levels in suppressing double bond isomerization without inhibiting dimerization. Moreover, since it is a liquid at room temperatures is easy to handle and dispense to the reaction mixture. Moreover, its low molecular weight means that for a given weight fraction, more mols of hexyne are present in the system than with larger molecules such as phenylacetylene. Also, unlike phenylacetylene, hexyne is non-carcinogenic.

The alkyne must be used in conjunction with the trialkylaluminum compound. That is, experimental work has shown that the alkyne is incapable of complexing or otherwise passivating the nickel in the absence of the trialkylaluminum compound. The mechanism by which the alkyne effects passivation of the nickel or otherwise overcomes the devastating effect nickel can have on dimer selectivity in the process is not known.

The effective nickel-passivation amounts of the alkyne hydrocarbon can be quite small, and will depend in large measure to the amount of nickel contamination to be encountered in the hot reaction mixture. In any given situation it is desirable to perform a few pilot experiments to determine the amount of alkyne that overcomes the adverse effect of the nickel that can be introduced into the reaction mixture by contact with nickel-containing surfaces, especially at elevated temperatures. Generally speaking, the amount used pursuant to this invention is enough to result in a dimer selectivity that is not more than 3 wt% (preferably not more than 2 wt%) less than the dimer selectivity achieved under absolutely identical conditions in a clean glass-lined reactor with the sole exception that in reaction performed in the glass-lined reactor, no alkyne is added. Most preferably the amount of alkyne used will give a dimer selectivity at least equal to, if not greater than, the dimer selectivity in the reaction performed in identical fashion (without alkyne addition) in the glass-lined reactor. Typically the amount introduced at the appropriate stage of the operation will not exceed about 5000 ppm (wt), and typically amounts in the range of up to about 2500 ppm are used. Normally, the smaller the amount sufficient to effectively inhibit double bond isomerization during dimerization, the better, as this minimizes costs and maximizes product purity. However any amount which provides the passivation under the conditions at hand without adversely affecting the dimer selectivity and vinylidene purity in any material way can be used.

Preferably the dimerization is conducted predominately (more than half of the reaction period) at one or more temperatures in the range of about 120° to about 180° C., more preferably in the range of above 140° to about 180° C., such as in the range of 160° to 170° C., in all such cases with reaction periods in the range of 1 to 24 hours sufficient to convert at least 10% (preferably at least 50% and more preferably at least 80%) by weight of the initial vinyl olefin to a different product. Reaction periods longer than 24 hours can be used, but are distinctly less desirable in a commercial operation. A particularly preferred embodiment involves conducting the dimerization predominately at temperatures in the range of about 165°±3° C. with reaction periods in the range of about 6 to about 12 hours sufficient to convert at least 85% by weight of the initial vinyl olefin to a different product.

The reaction should be conducted in an environment that is essentially anhydrous and substantially free of oxygen and air. Aluminum trialkyls can react violently with water or compounds containing hydroxyl groups such as alcohols. Thus even a small amount of water, alcohol, or the like, in the system will inactivate some of the aluminum trialkyl. If it known that some water is present in the vinyl olefin, by use of analysis such as Karl Fischer water analysis, the amount of aluminum alkyl catalyst can be increased to compensate for the water or other active hydrogen component such as alcohol whereby the proper amount of active aluminum trialkyl catalyst remains in the system even after part of the initial aluminum alkyl has been destroyed by the water or other active hydrogen compound. Alternatively, the olefin feed can be pretreated to remove water or alcohol contamination. Likewise the process should be conducted under a dry inert atmosphere e.g., nitrogen, argon, neon, or the like, to prevent catalyst destruction.

It is desirable to have good mixing in the reactor to ensure uniform temperature. In order to avoid high reactor skin temperature, it is desirable to set the temperature of the reactor heating medium at (or close to) the desired reaction temperature. Both heat from the heating medium and heat of reaction are utilized to bring the reaction mixture from room temperature to the reaction temperature. When the reactor temperature is higher than the temperature of the heating medium, the heat transfer direction will be reversed, i.e., from reaction mixture to the heating medium. Thus, the same heating medium at almost the same temperature may be used both as the heating medium during heat up to reaction temperature, and, as the cooling medium if and when the reaction temperature is passed. Either stem or other heating media such as Dowtherm may be used.

As noted above, in conducting the process of this invention the liquid mixture is maintained in direct contact with a nickel-containing metal alloy surface for at least one hour at a temperature above about 50° C., and at least one acetylenic hydrocarbon is added to the mixture prior to the time such contact occurs, the amount added being at least sufficient to inhibit nickel-induced double bond isomerization in the reaction mixture but insufficient to inhibit formation of the vinylidene dimer. The acetylenic hydrocarbon can be added to the mixture in any of a variety of ways. For example, the acetylenic hydrocarbon can be added to the vinyl olefin before the vinyl olefin is charged into the reactor and in this case the acetylenic hydrocarbon is carried into the reactor with the vinyl olefin before or at the same time the mixing with the trialkylaluminum compound occurs. Conversely, the acetylenic hydrocarbon can be added to the trialkylaluminum compound before the trialkylaluminum compound is charged into the reactor and in this case the acetylenic hydrocarbon is carried into the reactor with the trialkylaluminum compound before or at the same time the mixing with the vinyl olefin occurs. When using this procedure it is important to refrain from exposing the mixture of trialkylaluminum and acetylenic hydrocarbon to elevated temperatures that can cause chemical interaction between them. Another procedure is to form the mixture of the vinyl olefin and the trialkylaluminum compound and then add the acetylenic hydrocarbon to the resultant mixture. Still another approach is to concurrently feed each of these three ingredients into the reactor. Combinations of two or more such addition or mixing procedures can be utilized, if desired.

In an embodiment of this invention the mixture formed by the combining of the vinyl olefin, the trialkylaluminum and the acetylenic compound is maintained in at least one reactor in direct contact with steel alloy interior surfaces, especially nickel-containing steel alloy surfaces, for at least a major portion of the total period of time (and preferably all of the time) during which such reaction mixture is at a temperature above about 50° C.

In another embodiment, a process is provided in which:

1) a passivating amount of an acetylenic hydrocarbon is included in a mixture formed by combining vinyl olefin and trialkylaluminum in a ratio in the range of 0.001 to 0.5 mol of trialkylaluminum per mol of the initial vinyl olefin, and at a temperature below about 50° C. (most preferably at ambient temperatures below about 30° C.), to form a dimerization feed mixture which (a) contains a nickel impurity and/or (b) will be exposed before or during dimerization to at least one nickel-containing surface when at a temperature above about 50° C. for a time sufficient in the absence of the inclusion said acetylenic hydrocarbon to result in double bond isomerization and loss of dimer selectivity during dimerization; and 2) the dimerization mixture is heated at one or more temperatures in the range of about 100° to about 200° C. for a period of time sufficient to convert from 10 to about 99% by weight of the initial vinyl olefin to a different product with at least 80 % vinylidene dimer selectivity.

The passivating amount of the acetylenic hydrocarbon will usually be up to about 5000 parts by weight per million parts by weight of the mixture and, in any event, is at least sufficient to result in a dimer selectivity that is not more than 3 wt% less (preferably not more than 2% less, and more preferably not more than 1% less) then the dimer selectivity achieved under identical conditions in a clean glass-lined reactor and with no detectable nickel present either in the feed or in the reaction mixture. Generally speaking, the concentration of nickel impurity present in a reaction mixture sufficient to cause undesirable isomerization and loss of dimer selectivity at dimerization reaction temperatures in the range of 120° C. or above is about 2 or 3 ppm (wt) or less, and can be as little as 1 ppm or less.

Among suitable nickel-containing steels for use in fabricating the reactor are the so-called mild steels and low-alloy steels, as long as such steels do not contain so much nickel that 5000 ppm of the acetylenic hydrocarbon is incapable of suppressing double bond isomerization to no more 0.5 wt% more than the percentage by weight of double bond isomerized product formed under identical conditions in a scrupulously clean glass-lined reactor of identical interior volume using the same quantities of the same vinyl olefin and of the same trialkylaluminum compound in the absence of the acetylenic hydrocarbon.

Most preferably the steel or other metal alloy to which the reaction mixtures of this invention are exposed has been passivated by treatment with air or oxygen. To accomplish such passivation, the fresh (i.e., thoroughly clean) nickel-containing steel or alloy surfaces of the reactor and auxiliaries (feed lines, valves, stirrer parts, baffles, or the like) that come in contact with the reaction feeds and mixtures, especially when at temperatures above about 50° C., are exposed at temperatures in the range of about 25° C. to about 100° C. to contact with air or oxygen for a period sufficient to form at least a passivating molecular film of oxide on the exposed surfaces. The use of this procedure with ferrous metals and steel alloys is described in commonly-assigned copending application Ser. No. 08/596,801. (Case OL-6962), filed Feb. 5, 1996 (contemporaneously herewith), all disclosure of which is incorporated herein by reference as if fully set forth herein. Commonly-owned copending application Ser. No. 08/1596,848, (Case OL-6941) filed Feb. 5, 1996 (contemporaneously herewith) describes a dimerization process in which a combination of short reaction periods and low catalyst concentrations are used under specified temperature conditions.

For detailed specifications and chemical analyses of steels, references should be made to the ASTM Standards published by the American Society for Testing Materials. Appropriate publications by the American Society of Mechanical Engineers, the American National Standards Institute, and the American Petroleum Institute can be also be consulted, if necessary.

In conducting the process of this invention portions of the overall reaction system or train with which the feed and/or reaction mixture comes in contact when at temperatures of 50° C. or above can be composed of suitable materials other than nickel-containing steels or nickel alloys. Examples of such suitable materials include glass (e.g., glass-lining), nickel-free steels, and mild metals such as copper. However this invention makes it possible to use nickel-containing reactors and/or auxiliaries in a dimerization process without experiencing the devastating consequences on dimer selectivity that can result from exposure of the dimerization reaction mixture to non-passivated nickel-containing surfaces at elevated dimerization reaction temperatures. Also, the dire consequences of nickel-containing impurities in the feeds to the dimerization reaction can also be overcome by the practice of this invention.

To ensure the achievement of the full benefits of this invention, it is desirable to remove surface contamination such as previous reaction residues from the reactor surfaces, as well as other portions of the reaction system that come in contact with the feeds and/or reaction mixture. Clearly, any surface residues containing significant quantities of nickel should be thoroughly removed from contaminated surfaces. Likewise metal impurities in or on surfaces that contact the reactor feed or contents such as Na, Li, etc. may also enhance isomerization of vinyl olefins and should also be removed or, preferably, totally avoided wherever possible.

It will now be readily apparent that there are a number of things that should be done in order to achieve the optimum results achievable by the practice of this invention, especially when using reaction equipment that has been used previously for conducting other kinds of chemical reactions. Such matters are considered below.

Prior to feed transfer to the dimerization reactor, the reactor should be cleaned with aqueous and/or organic solvents. The pre-reaction cleanup procedures may include some of the following steps: A) Caustic or acidic wash; B) Water wash; C) Drying (removal of water); D) Heptane (or other heavy paraffin/olefin) wash; and E) Drying (removal of heptane or other heavy paraffin/olefin.) Caustic or acidic washing may introduce trace amount of impurities either from the solution or from leaching of material from the interior reactor surfaces. Therefore it is desirable to avoid use of caustic or acidic washing of reactor surfaces. In cases where hot organic solvent wash alone is sufficient to clean up the reactor, aqueous wash is not needed. But in cases where aqueous wash is needed to accomplish the reactor cleanup, use of steam cleaning or hot water wash without use of base or acid is preferred. Caustic or acidic wash should only be used if the other alternatives are inadequate in any given situation.

If the reactor history is such that caustic or acidic wash is needed, this should be followed with fresh water washes several times until the quality of final washed water is the same as (or close to) the fresh water used. This may be accomplished by measuring pH or ionic strength (such as Ni, Na, Cl etc.). Since trace amounts of isomerization promoters can reduce dimer yield tremendously, the purest water available at the plant site (e.g., deionized water or distilled water) is preferably used. After water wash is complete and the final wash water is discharged, the reactor should be blown to dryness with by nitrogen, as any residual water in the reactor will destroy the corresponding amount of aluminum alkyl catalyst. After aqueous wash of the reactor, organic solvent wash (heptane or others) should follow. Hot heptane wash for several hours under agitation conditions can expedite the organic wash process. After heptane wash and discharge of waste heptane, the reactor is preferably purged with nitrogen to dry the reactor. Nitrogen purge with some heat in the reactor accelerates the heptane drying process. If metal surface passivation is to be effected by use of air (or oxygen), the cleaned reactor and associated metallic equipment with which the feeds and reaction mixtures come in contact are exposed to air for at least 0.5 hour, preferably for from 0.5 to 3 hours at a temperature of at least about 20° C., such as ambient room temperature up to about 100° C. Shorter exposure periods can be used when employing pure oxygen for surface passivation.

After all of the heptane (or other heavy paraffin/olefin) is removed and the steel surfaces pacified by contact with air or oxygen (if this particular method of passivation has been used), the dimerization reactor should be maintained with 10 psig $N_2$ at room temperature. All further processing is performed under a blanket of dry inert gas, preferably a nitrogen blanket.

Whenever possible the feed transfer lines should be treated with the same diligence as the reactor pretreatment procedure to ensure that no contamination of feeds occurs from the transfer lines.

After the dimerization reactor and associated feed transfer lines have been cleaned up and pacified by contact with air or oxygen (if this method of passivation has been used), it is desirable to conduct a blank isomerization operation. This involves charging the reactor under a $N_2$ blanket or purge with vinyl olefin feed of the type to be used for dimerization. In the absence of trialkylaluminum catalyst; the olefin feed is then heated to 165° C. and kept at that temperature for about 12 hours. Such a blank isomerization test makes it possible to determine if there is any isomerization activity in the system in the absence of the trialkylaluminum catalyst. Pilot plant experience has indicated that there is no isomerization in the above glass-lined reactor during the blank isomerization test even if coupons of carbon steel and/or stainless steel coupons are present in the reactor.

If heavy olefin such as tetradecene is used in the reactor pretreatment, a blank isomerization test can be also carried out with the hot heavy olefin during the reactor cleanup.

The reactor must pass a blank isomerization test before proceeding to dimerization. If it does not, the reactor can be cooked for another 24–48 hours using the same olefin to remove any residual materials which may not be completely removed during the reactor pretreatment. Then another blank isomerization test should be conducted using another fresh charge of the olefin feed. If this blank isomerization test still fails, further investigation is required to determine the cause. In this connection, failure in a blank isomerization test is deemed to be the formation in the olefin of 0.5% by weight or more of internal olefin as determined by NMR.

After achieving a satisfactory blank isomerization test; the specified amount of trialkylaluminum is charged and mixed with the vinyl olefin in the reactor containing 90 wt% of the specified total amount olefin feed to be used in the reaction. Then the remaining amount of vinyl olefin (10 wt% of specified total olefin feed) is charged to flush out any trialkylaluminum which may be trapped in the feed transfer line. The specified quantity of alkyne hydrocarbon is introduced before, during or after the trialkylaluminum is charged.

A preferred series of process steps includes: A) Batch dimerization; B) Caustic wash; C) Phase separation; and D) Distillation. These steps are briefly discussed below.

Batch dimerization is most preferably carried out at 165° C. using substantially pure linear alpha-olefin (LAO) as the vinyl olefin feed and a charge of triethylaluminum (TEA) (preferably a low hydride grade) as the catalyst. At a TEA/LAO feed molar ratio of 0.0167, reaction under these conditions typically achieves 90% LAO conversion in 12 hours reaction time. During the dimerization of an alpha-olefin (e.g., 1-octene); TEA will be converted at least in part to trialkylaluminum in which the alkyl groups correspond to the alpha-olefin (in this example, to tri-n-octyl aluminum).

In conducting the dimerization reactions of this invention it is desirable to have a low volume of vapor space to minimize isomerization in the vapor phase which in turn can reduce selectivity to dimer formation. In general the vapor space or free space in the reactor will fall in the range of 0 to 40%. Preferably, the feed charge is such that at reaction temperature, the liquid phase occupies at least 70%, more preferably over 80%, still more preferably 90% or more, and most preferably at least about 95% or more, of the internal reactor volume.

The catalyst can be, and preferably is, recovered from the reaction product and recycled to the dimerization reactor.

The following Examples illustrate the results and advantages that can be achieved by the practice of this invention as well as the importance of the operating conditions and materials used pursuant to this invention. As indicated, these Examples are intended to illustrate, and should be understood to illustrate, and not limit this invention. All reactions in these Examples reactions were conducted in a two-liter, three-necked glassware reactor in order to clearly demonstrate the process features under evaluation. The reactor was equipped with an overhead total condenser. All runs were performed with continuous agitation under dry nitrogen atmospheres. The runs were conducted for 20–22 hours. In the examples, all parts and percentages are by weight unless otherwise specified.

EXAMPLE 1

Six consecutive dimerization runs were carried out as control runs—i.e., no alkyne was used. In each case 1-decene was dimerized using triethylaluminum at a ratio of 0.01 mol of triethylaluminum per mol of 1-decene. The reaction temperature was 165° C. in each run. To the feed in the first run of this series was added 8 ppm (wt) of nickel in the form of nickel acetylacetonate dissolved in 1-decene. No additional nickel was added in the next five runs of this series. After runs 1, 2 and 3 the reactor was drained, washed with heptane, drained again, and allowed to dry under a nitrogen atmosphere. After conducting runs 4 and 5, the reactor was drained, washed with 20% concentrated HCl (for 20 minutes before run 5 and for 2 hours before run 6), drained, washed with heptane, drained again, and allowed to dry under a nitrogen atmosphere. The products from each of these runs were analyzed and the selectivity to dimer formation was thereby determined. Table 1 summarizes these results.

TABLE 1

| Run No. | Pre-Reaction Procedure | Dimer Selectivity, % |
|---|---|---|
| 1 | 8 ppm Ni added | 1.8 |
| 2 | Heptane wash | 3.8 |
| 3 | Heptane wash | 5.8 |
| 4 | Heptane wash | 7.7 |
| 5 | HCl and Heptane washes | 27.1 |
| 6 | HCl and Heptane washes | 57.8 |

It can be seen from Table 1 that the presence of nickel had a devastating effect upon dimer selectivity (runs 1–6), that the dilution and heptane washes had little beneficial effect (runs 2–4), and that while the combination of HCl and heptane washes did improve dimer selectivity, it was still unsatisfactory (runs 5 and 6). Clearly the amount of nickel remaining after the second HCl wash (before runs 6) must have been very low, and yet the results were unsatisfactory. This underscores the difficulty in eliminating the deleterious effect and persistent adverse carry over effect of nickel in the aluminum alkyl catalyzed dimerization reaction.

EXAMPLE 2

Next a series of three runs was conducted. In each case 1-decene was dimerized using triethylaluminum at a ratio of 0.01 mol of triethylaluminum per mol of 1-decene. The reaction temperature was 165° C. in each run. To the feed in the first nm of this series (run 7) was added 8 ppm (wt) of nickel in the form of nickel acetylacetonate dissolved in 1-decene. No additional nickel was added in the next two runs of this series. Before each of these runs 160 ppm of hexyne was added to the reaction mixture, and after each run the reactor was drained, washed with heptane, drained again, and allowed to dry under a nitrogen atmosphere. The products from each of these runs were analyzed and the selectivity to dimer formation was thereby determined. Table 2 summarizes these results.

TABLE 2

| Run No. | Pre-Reaction Procedure | Dimer Selectivity, % |
|---|---|---|
| 7 | 8 ppm Ni & 160 ppm hexyne added | 0.5 |
| 8 | Heptane wash; 160 ppm hexyne added | 61.4 |
| 9 | Heptane wash; 160 ppm hexyne added | 78.5 |

It can be seen from Table 2 that in run 7 the amount hexyne used was insufficient to overcome the devastating effect of the nickel present in that run. In run 8 a great increase in dimer selectivity was achieved through the addition of the hexyne, although the result was still not completely satisfactory because the amount of hexyne used was insufficient to overcome the adverse carryover effect of the nickel. However in run 9 the hexyne overcame the nickel carryover effect and gave a satisfactory result.

EXAMPLE 3

A pair of runs was conducted as in Example 2 except that 8 ppm of nickel and 1000 ppm of hexyne were added to the reaction mixture before conducting the dimerization reaction of run 10. In run 11 no additional nickel was added and instead, 1000 ppm of hexyne was added to the reaction mixture before conducting the dimerization reaction. The results are summarized in Table 3.

TABLE 3

| Run No. | Pre-Reaction Procedure | Dimer Selectivity, % |
|---|---|---|
| 10 | 8 ppm Ni & 1000 ppm hexyne added | 0.9 |
| 11 | Heptane wash; 1000 ppm hexyne added | 88.7 |

The results in Table 3 indicate that although in run 10 the amount hexyne used was insufficient to overcome the devastating effect of the nickel present, in run 11 the hexyne dramatically overcame the effect of the nickel.

Additional reactions were carried out with elemental nickel additions as the nickel source instead of the nickel acetylacetonate. The results were similar to those presented in the above examples.

Each and every patent or other publication referred to in any portion of this specification is fully incorporated into this disclosure by reference as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process for producing vinylidene olefin using a trialkylaluminum compound as the sole catalyst component charged to the reactor, which process comprises forming and heating a mixture of vinyl olefin and at least one trialkylaluminum compound as the catalyst in a ratio in the range of 0.001 to 0.5 mol of trialkylaluminum per mol of the initial vinyl olefin at a temperature in the range of about 100° to about 200° C. for a period of time sufficient to convert from about 10 to about 99% by weight of the initial vinyl olefin to a different product with at least 80 wt % vinylidene dimer selectivity, said process being further characterized in that (i) said mixture is in direct contact with a nickel-containing metal alloy surface for at least one hour at a temperature above about 50° C., and (ii) at least one acetylenic hydrocarbon is added to said mixture prior to said contact in an amount at least sufficient to inhibit double bond isomerization in said reaction mixture but insufficient to inhibit formation of said vinylidene dimer.

2. A process of claim 1 wherein the acetylenic hydrocarbon in the form added to said mixture is an alkyne having in the range of from 4 to 10 carbon atoms per molecule and wherein the amount thereof added to said mixture is in the range of up to about 5000 parts by weight per million parts by weight of said mixture.

3. A process of claim 1 wherein the reactor is a single reactor in which the reaction is conducted with agitation on a batch basis, and wherein during at least 50 percent of the time that the reaction mixture is at a temperature above about 110° C. while in said reactor:
   a) the vapor space in the reactor is in the range of 0 to 40 percent of the total interior free space of the reactor, and
   b) the remainder of the free space in the reactor contains an inert atmosphere.

4. A process of claim 1 wherein the reactor is a single reactor in which the reaction is conducted with agitation on a batch basis, and wherein during substantially the entire time the time that the reaction mixture is at a temperature above about 110° C. while in the reactor:
   a) the vapor space in the reactor is in the range of 0 to 10 percent of the total interior free space of the reactor, and
   b) the remainder of the free space in the reactor contains an inert atmosphere.

5. A process of claim 1 wherein the reactor comprises at least two vessels in which the reaction is conducted with agitation and continuous feed, said vessels being connected in series such that the feed rate to the first vessel, and the discharge rates from each vessel to the ensuing vessel, where there is an ensuing vessel, are substantially equal to each other; and wherein during at least 50 percent of the time that the reaction mixture is at a temperature above about 110° C. while in said vessels:
   a) the vapor space in said vessels is in the range of 0 to 40 percent of the total interior free space of the vessels, and
   b) the remainder of the free space in said vessels contains an inert atmosphere.

6. A process of claim 1 wherein the reactor comprises at least two vessels in which the reaction is conducted with agitation and continuous feed, said vessels being connected in series such that the feed rate to the first vessel, and the discharge rates from each vessel to the ensuing vessel, where there is an ensuing vessel, are substantially equal to each other; and wherein during substantially the entire time that the reaction mixture is at a temperature above about 110° C. while in said vessels:
   a) the vapor space in each of said vessels is in the range of 0 to 10 percent of the total interior free space of that vessel, and
   b) the remainder of the free space in each said vessel contains an inert atmosphere.

7. A process of claim 1 wherein the reactor is a single continuous elongated reactor in which the reaction is conducted with agitation on a continuous basis, and wherein during at least 50 percent of the time the reaction mixture is at a temperature above about 110° C. while in said reactor:
   a) the vapor space in the reactor is in the range of 0 to 40 percent of the total interior free space of the reactor, and
   b) the remainder of the free space in the reactor contains an inert atmosphere.

8. A process of claim 1 wherein the reactor is a single continuous elongated reactor in which the reaction is conducted with agitation on a continuous basis, and wherein during substantially the entire time that the reaction mixture is at a temperature above about 110° C. while in said reactor:
   a) the vapor space in the reactor is in the range of 0 to 10 percent of the total interior free space of the reactor, and
   b) the remainder of the free space in the reactor contains an inert atmosphere.

9. A process of claim 1 wherein the trialkylaluminum as charged to the reaction vessel is one or more trialkylaluminum compounds in which substantially all of the alkyl groups are straight chain primary alkyl groups having in the range of from 2 to about 14 carbon atoms.

10. A process of claim 1 wherein the trialkylaluminum as charged to the reaction vessel contains, if any, a maximum of 0.10 wt % of aluminum hydride equivalent.

11. A process of claim 1 wherein the trialkylaluminum as charged to the reaction vessel is triethylaluminum.

12. A process of claim 11 wherein the triethylaluminum as charged to the reaction vessel contains, if any, a maximum of 0.10 wt % of aluminum hydride equivalent.

13. A process of claim 1 wherein the vinyl olefin charged to the reactor contains in the range of 3 to 20 carbon atoms per molecule, wherein the acetylenic hydrocarbon in the form added to said mixture is an alkyne having in the range of from 4 to 10 carbon atoms per molecule, and wherein the amount of alkyne added to said mixture is in the range of up to about 2500 parts by weight per million parts by weight of said mixture.

14. A process of claim 1 wherein said vinyl olefin is a single vinyl olefin, wherein the acetylenic hydrocarbon in the form added to said mixture is an alkyne having in the range of from 4 to 10 carbon atoms per molecule, and wherein the amount of alkyne added to said mixture is in the range of up to about 2500 parts by weight per million parts by weight of said mixture.

15. A process of claim 14 wherein said single vinyl olefin is in admixture with up to about 40 mol percent of internal and/or vinylidene olefins and wherein said alkyne is at least one straight chain hexyne isomer.

16. A process of claim 14 wherein said single vinyl olefin is in admixture with up to about 40 mol percent of a mixture of (a) internal and/or vinylidene olefins, and (b) one or more paraffinic hydrocarbons.

17. A process of claim 14 wherein said vinyl olefin is a mixture of two or more vinyl olefins.

18. A process of claim 17 wherein said mixture of vinyl olefins is in admixture with up to about 40 mol percent of internal and/or vinylidene olefins.

19. A process of claim 17 wherein said mixture of vinyl olefins is in admixture with up to about 40 mol percent of one or more paraffinic hydrocarbons.

20. A process of claim 17 wherein said mixture of vinyl olefins is in admixture with up to about 40 mol percent of a mixture of (a) internal and/or vinylidene olefins, and (b) one or more paraffinic hydrocarbons.

21. A process of claim 1 wherein the ratio of trialkylaluminum per mol of the initial vinyl olefin is in the range of about 0.005 to about 0.05 mol of trialkylaluminum per mol of the initial vinyl olefin.

22. A process of claim 1 wherein the ratio of trialkylaluminum per mol of the initial vinyl olefin is in the range of about 0.010 to about 0.05 mol of trialkylaluminum per mol of the initial vinyl olefin.

23. A process of claim 1 wherein the dimerization is conducted predominately at temperatures in the range of about 120° to about 180° C. with reaction periods in the range of 1 to 24 hours.

24. A process of claim 1 wherein the dimerization is conducted predominately at temperatures in the range of 145° to 170° C. with reaction periods in the range of 1 to 15 hours.

25. A process of claim 1 wherein the dimerization is conducted predominately at temperatures in the range of 160° to 170° C. with reaction periods in the range of about 6 to about 12 hours.

26. A process of claim 1 wherein at least 95 percent of the interior surfaces of the reactor that are in direct contact with the reaction mixture are composed of a nickel-containing steel alloy.

27. A process of claim 1 wherein the vinyl olefin charged to the reactor contains in the range of 4 to 20 carbon atoms per molecule, wherein the trialkylaluminum as charged to the reaction vessel is one or more trialkylaluminum compounds in which substantially all of the alkyl groups are straight chain primary alkyl groups having in the range of from 2 to about 20 carbon atoms, and wherein the trialkylaluminum as charged to the reaction vessel contains, if any, a maximum of 0.10 wt % of aluminum hydride equivalent.

28. A process of claim 27 wherein said ratio is in the range of about 0.005 to about 0.05 mol of trialkylaluminum per mol of the initial vinyl olefin, and wherein the dimerization is conducted predominately at temperatures in the range of 160° to 170° C. with reaction periods in the range of 6 to 15 hours.

29. A process of claim 28 wherein the trialkylaluminum as charged to the reaction vessel is triethylaluminum.

30. A process of claim 29 wherein the triethylaluminum as charged to the reaction vessel contains, if any, a maximum of 0.10 wt % of aluminum hydride equivalent.

31. A process of claim 27 wherein the reactor is a single reactor in which the reaction is conducted with agitation on a batch basis, and wherein during substantially the entire time that the reaction mixture is at a temperature above about 110° C. while in said reactor:
  a) the vapor space in the reactor is in the range of 0 to about 5 percent of the total interior free space of the reactor, and
  b) the remainder of the free space, if any, in the reactor contains an inert atmosphere.

32. A process of claim 27 wherein the reactor comprises at least two vessels in which the reaction is conducted with agitation and continuous feed, said vessels being connected in series such that the feed rate to the first vessel, and the discharge rates from each vessel to the ensuing vessel, where there is an ensuing vessel, are substantially equal to each other; and wherein during substantially the entire time that the reaction mixture is at a temperature above about 110° C. while in one or more of said vessels:
  a) the vapor space in said one or more of said vessels is in the range of 0 to about 5 percent of the total interior free space of the vessels, and
  b) the remainder of the free space, if any, in said one or more of said vessels contains an inert atmosphere.

33. A process of claim 27 wherein the reactor is a single continuous elongated reactor in which the reaction is conducted with agitation on a continuous basis; and wherein during substantially the entire time the reaction mixture is at a temperature above about 110° C. while in said reactor:
  a) the vapor space in the reactor is in the range of 0 to about 5 percent of the total interior free space of the reactor, and
  b) the remainder of the free space, if any, in the reactor contains an inert atmosphere.

34. A process for producing vinylidene olefin which comprises:
  A) forming a dimerization reaction feed mixture by mixing together at a temperature below about 50° C. and in any sequence (i) at least one vinyl olefin, (ii) at least one trialkylaluminum, and (iii) at least one acetylenic hydrocarbon such that the mixture has a ratio in the range of 0.001 to 0.5 mol of trialylaluminum per mol of the vinyl olefin, and a passivating amount in the range of up to about 5000 parts by weight of acetylenic hydrocarbon per million parts by weight of said mixture, said mixture being characterized in that the mixture contains a nickel impurity and/or the mixture will be exposed before or during dimerization to at least one nickel-containing surface when at a temperature above about 50° C. for a time sufficient in the absence of the inclusion said acetylenic hydrocarbon to result in double bond isomerization and loss of dimer selectivity during dimerization; and
  B) heating said feed mixture at one or more temperatures in the range of about 100° C. to about 200° C. for a period of time sufficient to convert from 10 to about 99% by weight of the vinyl olefin to a different product with at least 80% vinylidene dimer selectivity; said passivating amount being at least sufficient to result in a dimer selectivity that is not more than 3 wt % less than the dimer selectivity achieved under identical conditions in a clean glass-lined reactor and with no detectable nickel present either in the feed or in the reaction mixture.

35. A process of claim 34 wherein the acetylenic hydrocarbon used in forming said feed mixture is hexyne.

36. A process for producing vinylidene olefin which comprises heating at one or more dimerization temperatures in the range of about 100 °C. to about 200° C., a mixture formed by mixing together at a temperature below about 50° C. and in any sequence (i) at least one vinyl olefin, (ii) at least one trialkylaluminum, and (iii) at least one acetylenic hydrocarbon in proportions in the range of about 0.001 to about 0.5 mol of trialkylaluminum per mol of the vinyl olefin, and a passivating amount in the range of up to about 5000 parts by weight of acetylene hydrocarbon per million parts by weight of said mixture, said amount being at least sufficient to prevent more than 3 % loss of dimer selectivity due to the presence of nickel impurities in said mixture and/or nickel-containing surfaces with which said mixture comes in contact prior to or during the dimerization reaction.

* * * * *

UNITED STATES PATENT AND TRADEMARK OFFICE
CERTIFICATE OF CORRECTION

PATENT NO.: 5,663,469
DATED: September 2, 1997
INVENTOR(S): Doglas H. Krzystowczyk, Kaung-Far Lin It is certified that error appears in the above-identified patent and that said Letters Patent is hereby corrected as shown below:

Patent reads:

| Col. | Line | |
|---|---|---|
| | | On the title page, item [57], |
| | 16,-17, | in the "ABSTRACT" "in an mount" should read --in an amount-- |
| 2 | 53 | "passivating mount" should read --passivating amount-- |
| 7 | 25 | "Either stem" should read --Either steam-- |
| 8 | 61 | "Ser. No. 08/1596,848," should read --Ser. No. 08/596,848,-- |
| 12 | 16 | "the first nm of this series" should read --the first run of this series-- |

Signed and Sealed this

Twenty-fifth Day of November, 1997

*Attest:*

*Attesting Officer*

BRUCE LEHMAN

*Commissioner of Patents and Trademarks*